United States Patent [19]
Buttler et al.

[11] Patent Number: 5,687,100
[45] Date of Patent: Nov. 11, 1997

[54] VIBRATING TUBE DENSIMETER

[75] Inventors: Marc Allan Buttler, Estes Park; Andrew Timothy Patten; Charles Paul Stack, both of Louisville, all of Colo.

[73] Assignee: Micro Motion, Inc., Boulder, Colo.

[21] Appl. No.: 680,903

[22] Filed: Jul. 16, 1996

[51] Int. Cl.$^6$ .................................................. G01F 1/84
[52] U.S. Cl. .................. 364/558; 364/510; 73/32 A; 73/861.02; 73/861.03; 73/861.351; 73/861.352
[58] Field of Search ................ 73/861.02, 861.03, 73/861.351–861.357, 861.18, 32 A, 223, 3; 364/510, 571.03, 558

[56] References Cited

U.S. PATENT DOCUMENTS

| | | | |
|---|---|---|---|
| 4,876,879 | 10/1989 | Ruesch | 73/32 |
| 5,295,084 | 3/1994 | Arunachalam et al. | 364/558 |
| 5,473,949 | 12/1995 | Cage et al. | 73/861.38 |
| 5,497,665 | 3/1996 | Cage et al. | 73/861.38 |
| 5,497,666 | 3/1996 | Patten et al. | 73/861.38 |
| 5,602,346 | 2/1997 | Kitami et al. | 73/861.356 |

OTHER PUBLICATIONS

Numerical and Experimental Analysis of Coriolis Mass Flowmeters by Ian Darnell, Gregory M. Hulbert and Giles J. Brereton no date.

Coriolis–effect in mass flow metering by H. Raszillier and F. Durst. 1991.

Mylvaganam, K.S.; "Ultrasonic Gas Densitometer" IEEE, 24 Jan., 24, 1989.

Boyes Walt, "Practical Uses of Non–contacting Density Instrumentation"; Advances in Instrumentation and Control vol. 48, Part 2 Sep. 1993.

Blumenthal Joel "Direct mass flow rate and density monitoring using a Coriolis–gyroscopic sensor base"; Tappi Journal, vol. 68, No. 11 Dec. 1985.

Primary Examiner—Emanuel T. Voeltz
Assistant Examiner—Kamini Shah
Attorney, Agent, or Firm—Duft, Graziano & Forest, P.C.

[57] ABSTRACT

A Coriolis effect densimeter which produces density output data of improved accuracy by embodying the principal that the natural frequency of a vibrating tube filled with material decreases with an increase in the material mass flow rate. High accuracy output data is achieved by measuring the density and the mass flow rate of material through the vibrating tube, correcting the measured density to compensate for the effect of the mass flow rate, and correcting the mass flow rate correction of the density measurement for changes due to temperature.

30 Claims, 6 Drawing Sheets

VIBRATING TUBE DENSIMETER

FIELD OF THE INVENTION

This invention relates to a vibrating tube densimeter and, more particularly, to a Coriolis effect vibrating tube densimeter having density output data of increased accuracy and an increased range of operation.

STATEMENT OF THE PROBLEM

Early Coriolis effect densimeters, such as that disclosed in the U.S. Pat. No. 4,876,879 to Ruesch of Oct. 31, 1989, were designed and operated with the assumption that the accuracy of the density measurement is not affected by changes in the mass flow rate, temperature, viscosity or pressure of the measured fluid. Density measurement in a vibrating tube densimeter is based on a measurement of the natural frequency of vibration of the vibrating tube. Early densimeters were designed with the assumption that changes in the natural frequency of the driven flow tubes are only caused by changes in the density of the material flowing through the flow tube. The density measurement of these early densimeters was determined by these meters directly from the measured natural frequency.

A significant advance in densimeter theory and operation was provided in U.S. Pat. No. 5,295,084 to Aranachalam et al. of Mar. 15, 1994 which recognized that the natural frequency of a vibrating flow tube is affected by more than just the density of the fluid within the tube. It was noted analytically and experimentally that the natural frequency of a vibrating tube filled with flowing material decreases with an increase in the mass flow rate of the material in the vibrating tube. A density reading of increased accuracy was provided by measuring the natural frequency of the vibrating tube and correcting the measured natural frequency to compensate for the decrease in natural frequency caused by the mass flow rate of the material in the flow tube. The corrected natural frequency was then used in the standard density computation.

Experimentation and further development of the mathematical model disclosed in the Aranachalum patent exposed a shortcoming in the devices described by Aranachalum. The densimeter of Aranachalum is calibrated by developing three calibration constants. The first two calibration constants, calculated in the same way as was done by Ruesch, were used in the basic density measurement. However, rather than applying the measured tube frequency to the basic density measurement calculation, the third calibration constant was developed to compensate the measured tube frequency for the effect of mass flow rate. The compensated tube frequency is then applied to the basic density measurement calculation. The third calibration constant is determined by measuring the natural frequency of the vibrating tube while flowing a material of known density through the vibrating flow tube at a known mass flow rate. The change in tube frequency is thereby related to mass flow rate.

Analysis and experimentation have shown, however, that the decrease in the natural frequency due to the mass flow rate of material passing through the vibrating tube is itself dependant upon the density of the flowing material. In other words, at a given mass flow rate, the decrease in the natural frequency of the vibrating tube is different for materials of different density. The natural frequency of the vibrating tube will decrease more per unit of mass flow rate as materials with lower density are passed through the vibrating tube. In actual use, it is rare that a densimeter is used to measure the same flowing material on which the densimeter was calibrated.

There is a problem, therefore, with densimeters of the type described by Aranachalum. Although their density measurement is improved by an order of magnitude over earlier densimeters, their performance is degraded if, in operation, they are used to measure the density of flowing materials other than the material on which the densimeter was calibrated. There exists a need for a densimeter having a compensation for the effect of mass flow rate that is independent of the density of the measured material.

Another shortcoming of existing densimeters is the lack of compensation for the effect on existing density compensation schemes of changes in temperature. It is well known that the material properties of the vibrating flow tube change with temperature and this fact has been accounted for in Coriolis mass flowmeters since their inception as commercial devices. In particular, prior art Coriolis mass flowmeters compensate for changes in the Young's Modulus of the flow tube material due to changes in the temperature of the vibrating flow tube during operation of the Coriolis flowmeter. However, the Aranuchalum compensation scheme is itself affected by changes in temperature thereby degrading its performance.

There exists a need for a densimeter having improved performance characteristics. Namely, there exists a need for a densimeter which is compensated, independent of the density of the material being measured, for the effect of the mass flow rate of the material flowing through the vibrating tube. Also, there exists a need for a densimeter providing a density measurement compensation for the mass flow rate effect which is itself compensated for the effect on the compensation of changes in temperature.

STATEMENT OF THE SOLUTION

The above problems are solved and an advance in the art is achieved by the present invention which permits output data of high accuracy to be obtained from densimeters independent of the mass flow rate of material passing though them and independent of the temperature of the vibrating flow tube. The present invention provides a vibrating tube densimeter which delivers a density measurement which is compensated for effects of mass flow rate and temperature thereby improving density measurement performance to previously unattainable levels.

The basic theory of operation of vibrating tube densimeters is that the natural frequency of vibration of the vibrating tube or tubes changes with changes in density of the material being measured within the vibrating tube. The change in the natural frequency of the vibrating tube is tracked and related to the density of the measured fluid. It is known by researchers in this field that the natural frequency of a vibrating tube is effected by other factors in addition to changes in the density of the fluid flowing through the vibrating tube. The natural frequency of the vibrating tube decreases with increases in the mass flow rate of material through the vibrating tube. In addition, changes in temperature effect material properties of the vibrating tube and thus affect the natural frequency and mass flow rate effect or frequency of the vibrating tube.

A theoretical model that does consider the effect of mass flow rate of material flow through a vibrating tube was first applied to a commercial density measurement device in the invention of the Aranachalum patent. The model is set forth in an equation, known as Housner's Equation, which is a one-dimensional, fluid-elastic equation describing the undamped, transverse, free vibration of a flow tube containing flowing material as follows:

$$EI\frac{\partial^4 u}{\partial x^4} + (\rho_f A_f + \rho_s A_s)\frac{\partial^2 u}{\partial t^2} + 2\rho_f A_f V_o \frac{\partial^2 u}{\partial x \partial t} + \rho_f A_f V_o^2 \frac{\partial^2 u}{\partial x^2} = 0$$

where
- $E$ = Young's modulus of elasticity of the flow tube
- $I$ = moment of inertia of the flow tube
- $\rho_f$ = density of the material
- $\rho_s$ = density of the flow tube
- $A_f$ = cross-sectional area of the flow region
- $A_s$ = cross-sectional area of the flow tube
- $V_o$ = flow speed
- $u(x,t)$ = transverse displacement of the flow tube The mixed-partial derivative term is known as the Coriolis term of Housner's Equation. The second-order partial derivative with respect to the spatial variable (x) term is known as the centrifugal term of Housner's Equation. This model was used to develop the compensation scheme of the Aranachalum patent and its implementation in commercial densimeters provided an order of magnitude improvement in density measurement performance over densimeters existing at the time. However, given the complexity of Housner's Equation, its analytical solutions were limited to straight-tube densimeter geometries. Those straight-tube results were then extrapolated to curved-tube densimeter geometries. Although the resulting improvement in density measurement performance for curved-tube densimeter geometries was significant, the present invention provides further significant advances in densimeter performance by accounting for characteristics unique to curved-tube densimeter geometries.

The present invention utilizes new understanding of the theory of operation of a vibrating tube densimeter. This new understanding is embodied in a more accurate analytical model, as described below, which is used to provide a compensation which is independent of the density of the material to be measured, unlike the compensation provided by the Aranachalum patent.

In the case of a vibrating tube, whether straight or curved, one effect of material flowing through the tube is to produce forces which act on the tube. These forces are described by the Housner equation and include centrifugal forces and Coriolis forces. It is the centrifugal forces that are primarily responsible for the decrease in the vibrating tube's natural frequency with increasing mass flow rate. The Coriolis forces also play a role in causing the mass flow effect on natural frequency but it is the centrifugal forces that are the primary contributor. The type of these centrifugal forces is different, however, for straight and curved tubes.

Both straight and curved vibrating tubes experience what can be called dynamic centrifugal forces. Dynamic centrifugal forces are the result of the local curvature of the vibrating tube caused by the tube's vibration. A straight tube densimeter and a curved tube densimeter both operate through the vibration of their respective tubes and in each case the vibrating tube, whether straight or curved, is subject to the generated dynamic centrifugal forces. The effect that the dynamic centrifugal forces have on the natural frequency of vibrating tube is dependent on both the mass flow rate and the density of the fluid. It is the effect of the dynamic centrifugal force term of Housner's Equation that is compensated for by the density compensation scheme of the Aranachalum patent.

In the case of a densimeter, or Coriolis mass flowmeter, employing a curved tube, the bends in the curved tube introduce another type of centrifugal force, called a steady-state centrifugal force. Steady-state centrifugal forces are the result of the flowing material changing direction as it flows around the bends in the flow tube or tubes. Tensile forces are generated in response to the steady-state centrifugal forces. When the relevant components of these tensile forces are added to Housner's equation it is seen that the steady-state centrifugal forces, as represented by the tensile force term, exactly cancel the dynamic centrifugal forces. The steady-state centrifugal forces are not present in a straight-tube densimeter since there are no fixed bends in the tube. Therefore, the dynamic centrifugal forces are not canceled by the steady-state centrifugal forces in a straight-tube densimeter.

The following equation represents Housner's equation for a curved tube showing the addition of the relevant tensile force term.

$$EI\frac{\partial^4 u}{\partial x^4} + (\rho_f A_f + \rho_s A_s)\frac{\partial^2 u}{\partial t^2} + 2\rho_f A_f V_o \frac{\partial^2 u}{\partial x \partial t} + \rho_f A_f V_o^2 \frac{\partial^2 u}{\partial x^2} - T\frac{\partial^2 u}{\partial x^2} = 0$$

where $T \cong \rho_f A_f V_o^2$

The tensile force term (steady-state centrifugal forces) cancels the dynamic centrifugal force term to result in the following formulation of Housner's equation.

$$EI\frac{\partial^4 u}{\partial x^4} + (\rho_f A_f + \rho_s A_s)\frac{\partial^2 u}{\partial t^2} + 2\rho_f A_f V_o \frac{\partial^2 u}{\partial x \partial t} = 0$$

As noted above, the centrifugal forces, as opposed to the Coriolis forces, are primarily responsible for the effect on the vibrating tube's natural frequency caused by the mass flow rate of material through the tube. Since, in a curved-tube densimeter, the dynamic centrifugal forces and the steady-state centrifugal forces cancel one another, as just demonstrated, densimeters employing curved tubes are far less sensitive to the mass flow rate effect than are densimeters employing straight tubes because only the Coriolis force affects the density measurement.

In the compensation scheme of the Aranachalum patent, it is the effect of the dynamic centrifugal force and Coriolis forces on the vibrating tube that is compensated where the centrifugal forces are the dominant forces. The compensation provided by Aranachalum necessarily includes a dependency on density. This is because the Aranachalum compensation involves measuring the tube frequency, determining the tube period by calculating the reciprocal of the tube frequency, and multiplying the tube period by a factor which includes the measured volume flow rate. In a Coriolis densimeter, volume flow rate is determined, in part, using the measured density, therefore the Aranachalum density compensation includes an inherent dependency on the density of the measured material.

In the present invention, it is the effect of the Coriolis force on the vibrating tube, since the centrifugal forces cancel, for which the compensation is provided. The compensation factor provided and utilized by the present invention does not include a density term as part of the compensation factor. As a result, the density compensation provided by the present invention is not dependent on the density of the material to be measured. Therefore, applied to a curved tube densimeter, the present invention provides a density measurement which is not affected by the mass flow rate of material through the vibrating tube and the compensation itself is not affected by the density of the material being measured.

The method and apparatus of the present invention first determines the measured density using the density measurement calculation as described in the Ruesch patent:

$$D_m = K_2 T_m^2 (1 - t_c t_m) - K_1$$

where $D_m$ is the measured density of the material (g/cm³)
$T_m$ is the measured tube period (s)
$K_1$ is equal to $K_2 T_a^2 - D_a$
$K_2$ is equal to $d/(T_w^2 - T_a^2)$
$D_w$ is the density of water at the time of calibration (g/cm³)
$D_a$ is the density of air at the time of calibration (g/cm³)
d is $D_w - D_a$ (g/cm³)
$t_c$ is the temperature compensation factor ((% change in $T_m^2$/OC)/100)
$T_a$ is the tube period for air with no flow at the time of calibration, corrected to 0° C. (s)
$T_w$ is the tube period for water with no flow at the time of calibration, corrected to 0° C. (s)
$t_m$ is the measured temperature (°C.)

The measured density ($D_m$) is then corrected using a compensation factor $K_3$ as follows:

$$D_c = D_m - K_3 (M_m)^2$$

where:

$D_m$ is the measured density (g/cm³)
$D_c$ is the compensated density (g/cm³)
$M_m$ is the measured mass flow rate (g/s)
$K_3$ is equal to $$D_{k3}/(M_{k3}^2)$$

$D_{k3}$ (g/cm³) is the error in the measured density during calibration at mass flow rate $M_{k3}$ (g/s). $K_3$ is determined during the calibration procedure by measuring the error in the density reading at a known mass flow rate. A corrected density is thus derived from the measured density.

A further advantage of the present invention is that the compensation scheme just described can be modified so that the mass flow rate effect compensation for density is itself compensated for the effect of temperature. It has been determined experimentally and analytically that the density measurement error due to the effect of mass flow rate also changes with temperature. The present invention provides a compensation for this temperature effect.

An additional calibration constant, $K_4$, is defined as follows:

$$K_4 = [D_{k4}/(K_3 \times M_{k4}^2) - 1]/(t_{k4} - t_{k3})$$

where $D_{K4}$ is the error in the measured density ($D_m$) at temperature $t_{K4}$ and mass flow rate $M_{K4}$.
$K_3$ is the calibration constant previously defined
$t_{K3}$ is the temperature at which $K_3$ was determined (°C.)
$t_{K4}$ is the temperature at which $K_4$ was determined (°C.)
$M_{K4}$ is the mass flow rate at which $K_4$ was determined (g/s)

$K_4$ is used to adjust the value of $K_3$ for deviations in operating temperature from the temperature at which $K_3$ was determined. After determining $K_3$ during the calibration process, as described above, $K_4$ is determined by changing the temperature of the flowing material and again measuring the density of the flowing material. The change in temperature results in an error in the compensated density measurement and $K_4$ is calculated as just described.

The calibration constant $K_4$ is used in operation of the present invention to adjust the value of $K_3$ as follows:

$$D_c = D_m - K_3 (1 + K_4 (t_m - t_{k3}))(M_m)^2$$

Where:

$D_m$ is the measured density (g/cc)
$D_c$ is the corrected density (g/cc)
$M_m$ is the measured mass flow rate (g/s)
$t_m$ is the measured temperature (°C.)
$t_{k3}$ is the temperature at which $K_3$ was calculated (°C.)
$K_3$ and $K_4$ as previously defined $K_4$ thus operates to linearize the effect of temperature on the $K_3$ compensation factor.

In accordance with the present invention, the output of the sensor apparatus connected to or associated with a vibrating flow tube (or tubes) is connected to signal processing circuitry which generates data indicating the measured density of the material flowing through the vibrating tube. The signal processing circuitry takes into account the fact that the measured density does not remain constant with changes in the mass flow rate of the material to be measured and/or the temperature of the vibrating tube. In so doing, the signal processing circuitry corrects the measured density and produces an output specifying a corrected density which is independent of the mass flow rate of the material whose density is measured. The mass flow rate compensation factor is itself compensated for changes in temperature of the vibrating tube. The methods of the present invention are optimally applied to curved-tube densimeters but can also be applied to straight-tube densimeters.

DETAILED DESCRIPTION

One possible preferred exemplary embodiment is illustrated in FIGS. 1 through 7. It is to be expressly understood that the present invention is not to be limited to this exemplary embodiment. Other embodiments and modifications are considered to be within the scope of the claimed inventive concept. The present invention can be practiced with other types of meters than the described meter. Successful implementation of the present invention is not dependent on any meter geometry although optional implementation is obtained in curved tube densimeters.

Figure 1:
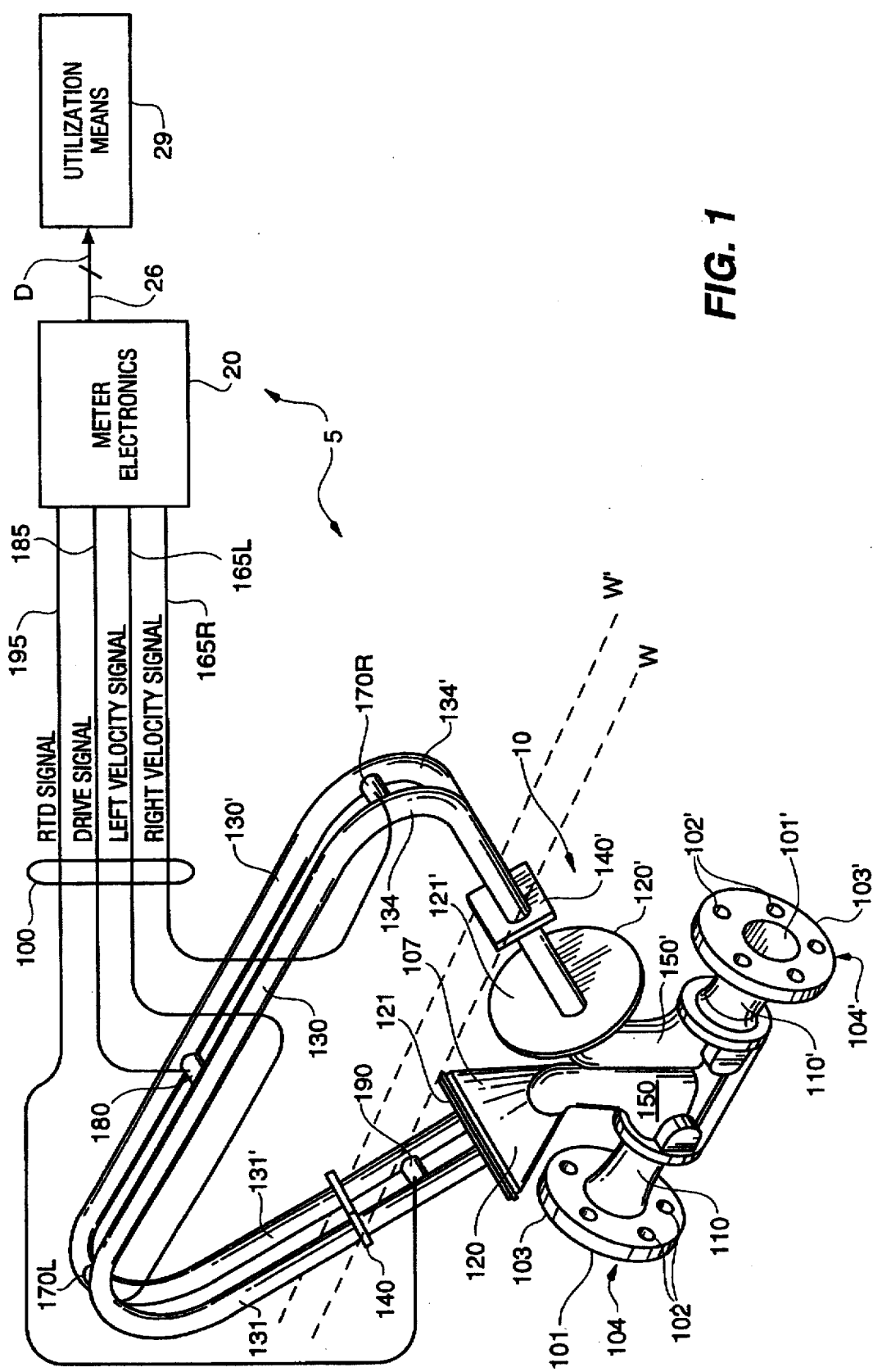
FIG. 1 discloses one possible exemplary embodiment of the invention.

Description of General System (FIG. 1)

FIG. 1 shows a Coriolis densimeter 5 comprising a Coriolis meter assembly 10 and meter electronics 20. Meter assembly 10 responds to mass flow rate and density of a process material. Meter electronics 20 is connected to meter assembly 10 via leads 100 to provide density, mass flow rate, and temperature information over path 26, as well as other information not relevant to the present invention. A Coriolis flowmeter structure is described although it is apparent to those skilled in the art that the present invention could be practiced as a vibrating tube densimeter without the additional measurement capability provided by a Coriolis mass flowmeter.

A Coriolis densimeter is convenient and preferred because it inherently provides the mass flow rate information necessary, as described below, for operation of the present invention. If a non-Coriolis, vibrating tube densimeter is used, the mass flow rate information needs to be input from a separate source of that information.

Meter assembly 10 includes a pair of manifolds 150 and 150', flanges 103 and 103' having flange necks 110 and 110', a pair of parallel flow tubes 130 and 130', drive mechanism 180, temperature sensor 190, and a pair of velocity sensors $170_L$ and $170_R$. Flow tubes 130 and 130' have two essentially straight inlet legs 131 and 131' and outlet legs 134 and 134' which converge towards each other at flow tube mounting blocks 120 and 120'. Flow tubes 130 and 130' bend at two symmetrical locations along their length and are essentially parallel throughout their length. Brace bars 140 and 140' serve to define the axis W and W' about which each flow tube oscillates.

The side legs 131, 131' and 134, 134' of flow tubes 130 and 130' are fixedly attached to flow tube mounting blocks 120 and 120' and these blocks, in turn, are fixedly attached to manifolds 150 and 150'. This provides a continuous closed material path through Coriolis meter assembly 10.

When flanges 103 and 103', having holes 102 and 102' are connected, via inlet end 104 and outlet end 104' into a flow tube system (not shown) which carries the process material that is being measured, material enters end 104 of the meter through an orifice 101 in flange 103 is conducted through manifold 150 to flow tube mounting block 120 having a surface 121. Within manifold 150 the material is divided and routed through flow tubes 130 and 130'. Upon exiting flow tubes 130 and 130', the process material is recombined in a single stream within manifold 150' and is thereafter routed to exit end 104' connected by flange 103' having bolt holes 102' to the flow tube system (not shown).

Flow tubes 130 and 130' are selected and appropriately mounted to the flow tube mounting blocks 120 and 120' so as to have substantially the same mass distribution, moments of inertia and Young's moduli about bending axes W—W and W'—W', respectively. These bending axes go through brace bars 140 and 140'. Inasmuch as the Young's moduli of the flow tubes change with temperature, and this change affects the calculation of flow and density, resistive temperature detector (RTD) 190 (typically a platinum RTD device) is mounted to flow tube 130', to continuously measure the temperature of the flow tube. The temperature of the flow tube and hence the voltage appearing across the RTD for a given current passing therethrough is governed by the temperature of the material passing through the flow tube. The temperature dependent voltage appearing across the RTD is used in a well known method by meter electronics 20 to compensate for the change in elastic modulus of flow tubes 130 and 130' due to any changes in flow tube temperature. The tube temperature is also used, according to the present invention, to compensate the mass flow rate and density compensation for changes in the temperature of the vibrating tube. The RTD is connected to meter electronics 20 by lead 195.

Both flow tubes 130 and 130' are driven by driver 180 in opposite directions about their respective bending axes W and W' and at what is termed the first out-of-phase natural frequency of the flowmeter. Both flow tubes 130 and 130' vibrate as the tines of a tuning fork. This drive mechanism 180 may comprise any one of many well known arrangements, such as a magnet mounted to flow tube 130' and an opposing coil mounted to flow tube 130 and through which an alternating current is passed for vibrating both flow tubes. A suitable drive signal is applied by meter electronics 20, via lead 185, to drive mechanism 180.

Meter electronics 20 receives the RTD temperature signal on lead 195, and the left and right velocity signals appearing on leads $165_L$ and $165_R$, respectively. Meter electronics 20 produces the drive signal appearing on lead 185 to drive element 180 and vibrate tubes 130 and 130'. Meter electronics 20 processes the left and right velocity signals and the RTD signal to compute the mass flow rate and the density of the material passing through meter assembly 10. This information, along with other information, is applied by meter electronics 20 over path 26 to utilization means 29. In determining the density, electronics 20 corrects the measured density of the material passing through tubes 130 and 130' in the manner taught by the present invention.

Figure 2:
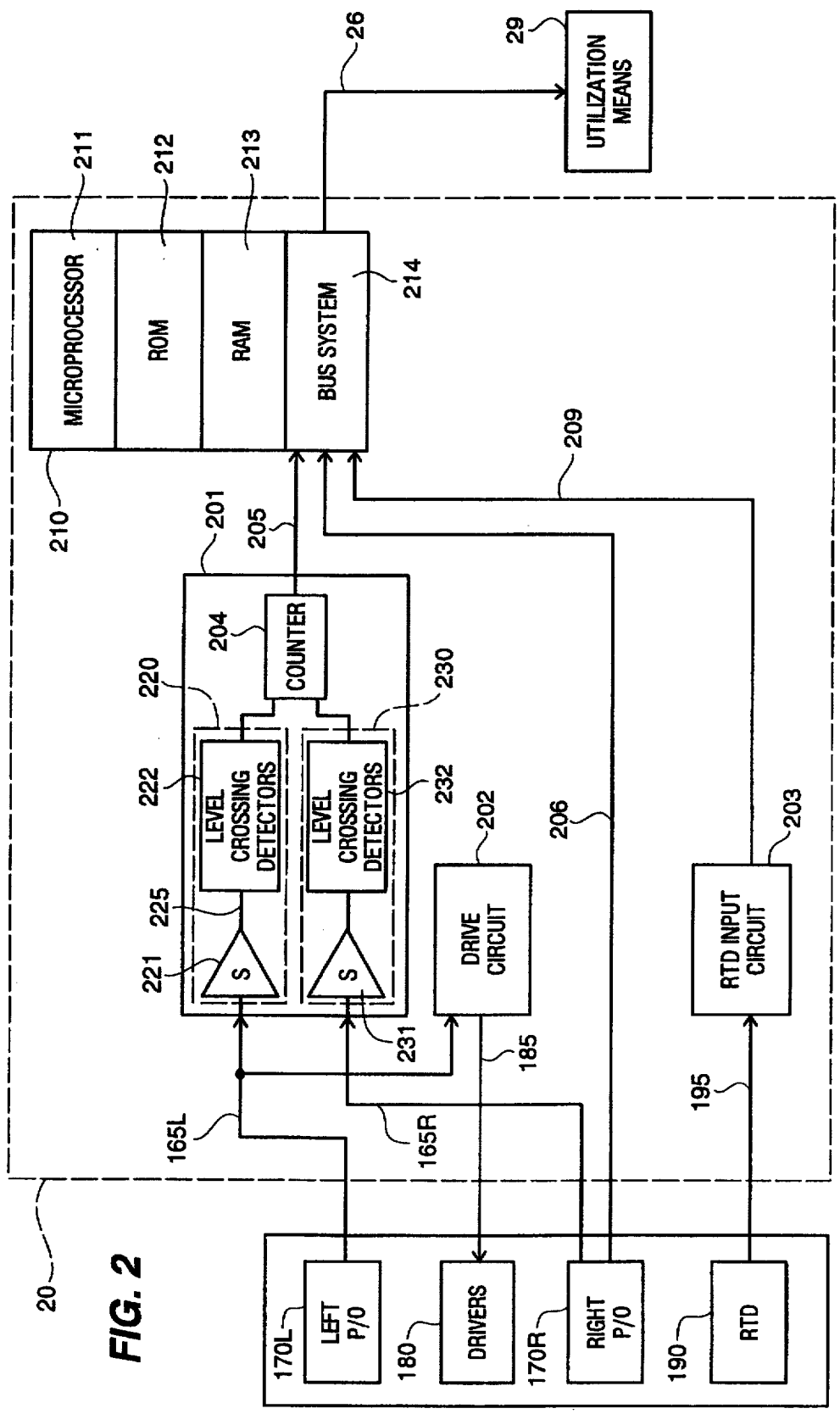
FIG. 2 discloses further details of the meter electronics 20 of FIG. 1.

Description of Meter Electronics (FIG. 2)

A block diagram of meter electronics 20 is shown in FIG. 2 as comprising mass flow measurement circuit 201, flow tube drive circuit 202, density measurement processing circuitry 210, and RTD input circuit 203.

Flow tube drive circuit 202 provides a repetitive alternating or pulsed drive signal via lead 185 to drive mechanism 180. Drive circuit 202 synchronizes the drive signal to the left velocity signal on lead $165_L$ and maintains both flow tubes 130 and 130' in opposing sinusoidal vibratory motion at their fundamental natural frequency. This frequency is governed by a number of factors, including characteristics of the tubes and the density and mass flow rate of the material flowing therethrough. Since circuit 202 is known in the art and its specific implementation does not form any part of the present invention, it is not discussed herein in further detail. The reader is illustratively referred to U.S. Pat. Nos. 5,009,109 (issued to P. Kalotay et al. on Apr. 23, 1991); 4,934,196 (issued to P. Romano on Jun. 19, 1990) and 4,876,879 (issued to J. Ruesch on Oct. 31, 1989) for a further description of different embodiments for the flow tube drive circuit.

The signals generated by sensors $170_L$ and $170_R$ can be processed in meter electronics 20, and in particular in mass flow measurement circuit 201, by any one of a number of well known methods to compute the mass flow rate of the material passing through the meter. One method of these approaches is depicted in FIG. 2. Mass flow measurement circuit 201 contains two separate input channels: left channel 220 and right channel 230. Each channel contains an integrator and two level crossing detectors. Within both channels, the left and right velocity signals from left and right pick-offs 170L and 170R are applied to respective integrators 221 and 231, each of which effectively forms a low pass filter. The outputs of integrators 221 and 231 are applied to level crossing detectors (effectively comparators) 222 and 232, which generate level change signals whenever the corresponding integrated velocity signal exceeds a voltage window defined by a small predefined positive and negative voltage level, e.g. ±2.5V. The outputs of level crossing detectors 222 and 232 are fed as control signals to counter 204 to measure a timing interval, in terms of clock pulse counts, that occurs between corresponding changes in these outputs. This interval is representative of the phase difference between the signal generated by left pick-off 170L and the signal generated by right pick-off 170R. The phase difference between these two signals is proportional to the mass flow rate of material flowing through tubes 130 and 130'. This value representative of phase difference, in counts, is applied as input data over path 205 to processing circuitry 210.

The computation of the mass flow rate and volume flow rate of the material passing through the tubes 130 and 130' can be accomplished by any of several known methods. These additional approaches to the calculation of mass flow rate are known by those skilled in the art and the reader is therefore illustratively referred to the following patents for a further description of the mass flow computation: U.S. Pat. Re 31,450 issued to Smith on Feb. 11, 1982; U.S. Pat. No. 5,231,884 issued to Zolock on Aug. 3, 1993 and U.S. Pat. 4,914,956 issued to Young, et al., on Apr. 10, 1990.

The natural frequency of vibration of flow tubes 130 and 130' is measured by monitoring the signal from one of the pick-offs. The signal from right pick-off 170R is fed over path 206 to processing circuitry 210. Processing circuitry 210 is operable to count the frequency output from right pick-off 170R to determine the frequency of vibration of vibrating tubes 130 and 130'.

Temperature element RTD 190 is connected by path 195 to RTD input circuit 203 which supplies a constant current to the RTD element 190, linearizes the voltage that appears across the RTD element and converts this voltage using a voltage to frequency converter (not shown) into a stream of pulses that has a scaled frequency which varies proportionally with any changes in RTD voltage. The resulting pulse stream produced by circuit 203 is applied over path 209 as an input to processing circuit 210.

Density measurement processing circuitry 210 on FIG. 2 includes microprocessor 211 and memory elements including a ROM memory 212 and a RAM memory 213. ROM 212 stores permanent information that is used by microprocessor 211 in performing its functions while RAM memory 213 stores temporary information used by microprocessor 211. The microprocessor together with its ROM and RAM memories and bus system 214 control the overall functions of the processing circuitry 210 so that it can receive input signals, as described herein, and process them in the manner required to apply, over path 26 to utilization means 29, the various items of data the Coriolis effect densimeter of the present invention generates. Processing circuitry 210 periodically updates the information available at utilization means 29. The information applied to utilization means 29 over path 26 includes mass flow rate, volume flow rate and density information. Utilization means 29 may either comprise a meter for a visual display of the generated density information or, alternatively, may comprise a process control system that is controlled by the density signal on path 26.

Processing circuitry 210, including microprocessor 211 together with memory elements 212 and 213, operate in accordance with the present invention to provide highly accurate density information. As subsequently described in detail in connection with the flow charts of FIGS. 4 and 5, this highly accurate density information is derived by the steps of measuring the natural frequency of the vibrating tubes from the signals provided by the velocity sensors 170L and 170R, calculating the measured density according to a known formulation and correcting this measured density to compensate for the fact that the measured density changes with changes in the mass flow rate of material flowing through tubes 130 and 130' and with changes in the temperature of tubes 130 and 130'. This density output data is of far greater accuracy than would be the case if the measured density was not corrected or if the natural frequency was corrected rather than the density.

Figure 3:
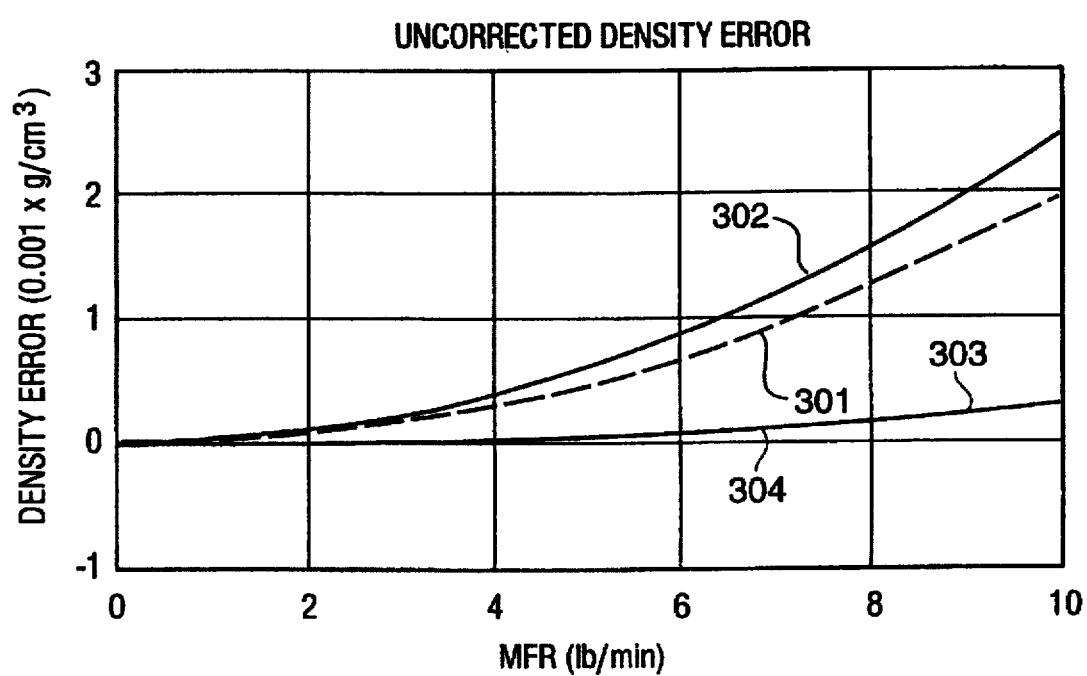
FIG. 3 is a graph illustrating the measured density error/mass flow rate relationship of a vibrating tube densimeter.

Mass Flow Rate Effect on Density Measurement
(FIG. 3)

As noted above, the natural frequency of an oscillating tube decreases as the mass flow rate of the material flowing through the tube increases. This effect directly impacts the measured density as the basic density measurement depends on the relationship between tube frequency and density.

FIG. 3 demonstrates the impact of mass flow rate on the accuracy of the density measurement. The vertical axis of FIG. 3 corresponds to the density error, represented in 0.001 g/cm$^3$. The horizontal axis is labeled in pounds per minute (lbs/min) of mass flow rate. Lines 301 and 302 are representative of the mass flow rate effect for a straight-tube densimeter geometry. Line 301 is representative of the error in density measurement over a range of mass flow rates for a flowing material having density of 1.194 specific gravity units (SGU). Line 302 is representative of the error in density measurement over a range of mass flow rates for a flowing material having a density of 0.994 SGU. In both cases, the physical vibrating structure is the same. It is only the flowing material within the vibrating tubes that is different. FIG. 3 demonstrates that the density measurement is dependant on the mass flow rate of the material flowing through the tube. Lines 301 and 302 demonstrate that, for a straight-tube densimeter, the dependance on mass flow rate is different for materials of different densities. Lines 303 and 304 are representative of the mass flow rate effect on density for a curved-tube densimeter having a similar flow capacity to the straight-tube densimeter used to generate the data of lines 301 and 302. As noted above, the resonant frequency of a curved-tube densimeter is less sensitive to the mass flow rate effect than is a straight-tube densimeter and this is illustrated in FIG. 3. Line 303 represents data for the same fluid as line 301 (1.194SGU) and line 304 represents data for the same fluid as line 302 (0.994SGU). As is evident in FIG. 3, the data of line 303 is indistinguishable from the data of line 304 illustrating the fact that, in a curved-tube densimeter, the error in density reading due to mass flow rate does not change for fluids of different densities.

Figure 6:
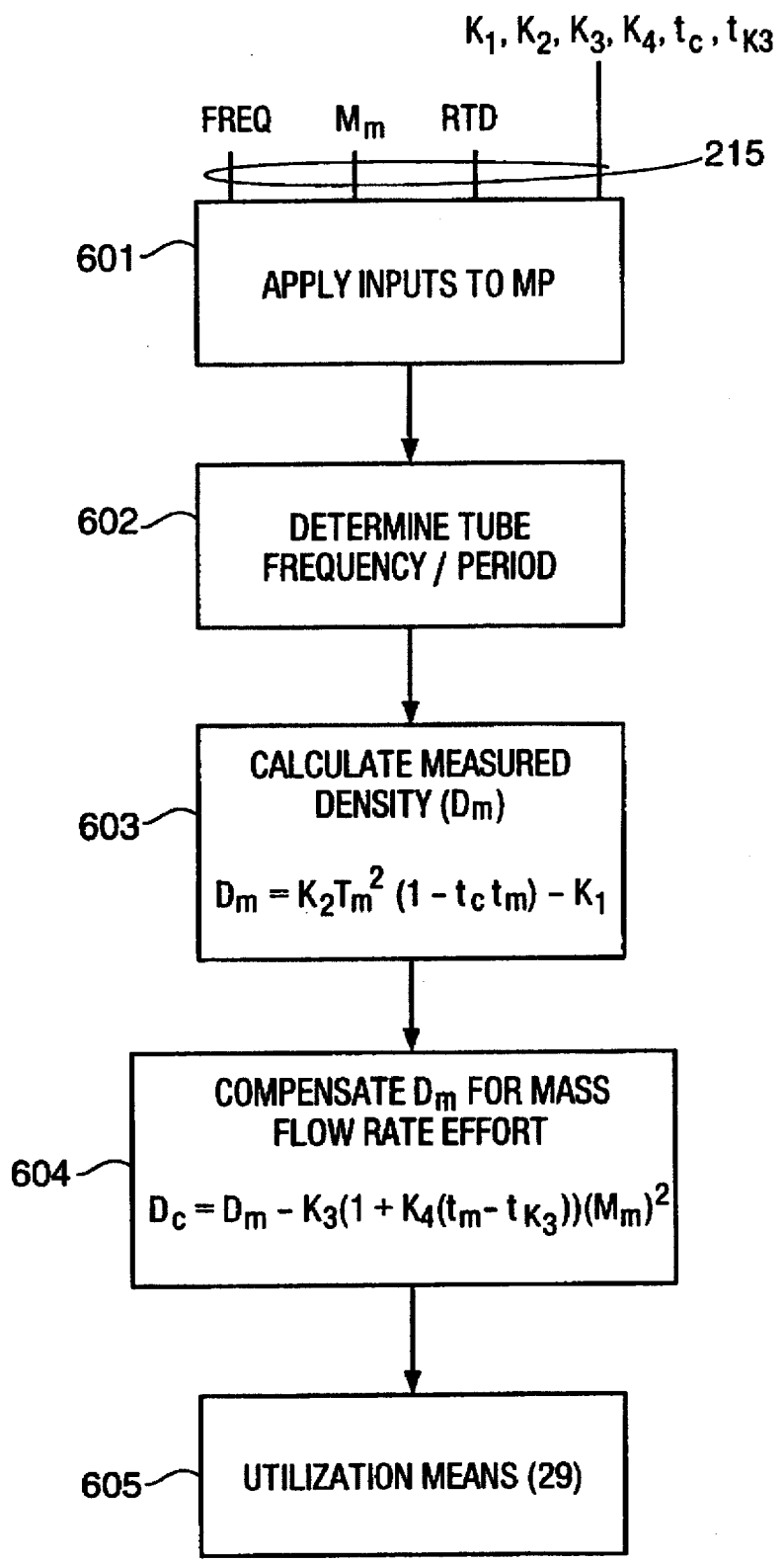
FIG. 6 is a flow chart describing the operation of the meter electronics 20 and its processing circuitry 210 as it measures the density and corrects the measured density for the effect on the density measurement by mass flow rate taking into account the temperature dependence of the effect.

The effect on the density measurement by the temperature of the vibrating tube is not depicted in FIG. 3. FIG. 6 discussed below demonstrates the combined effects of mass flow rate and temperature.

Figure 4:
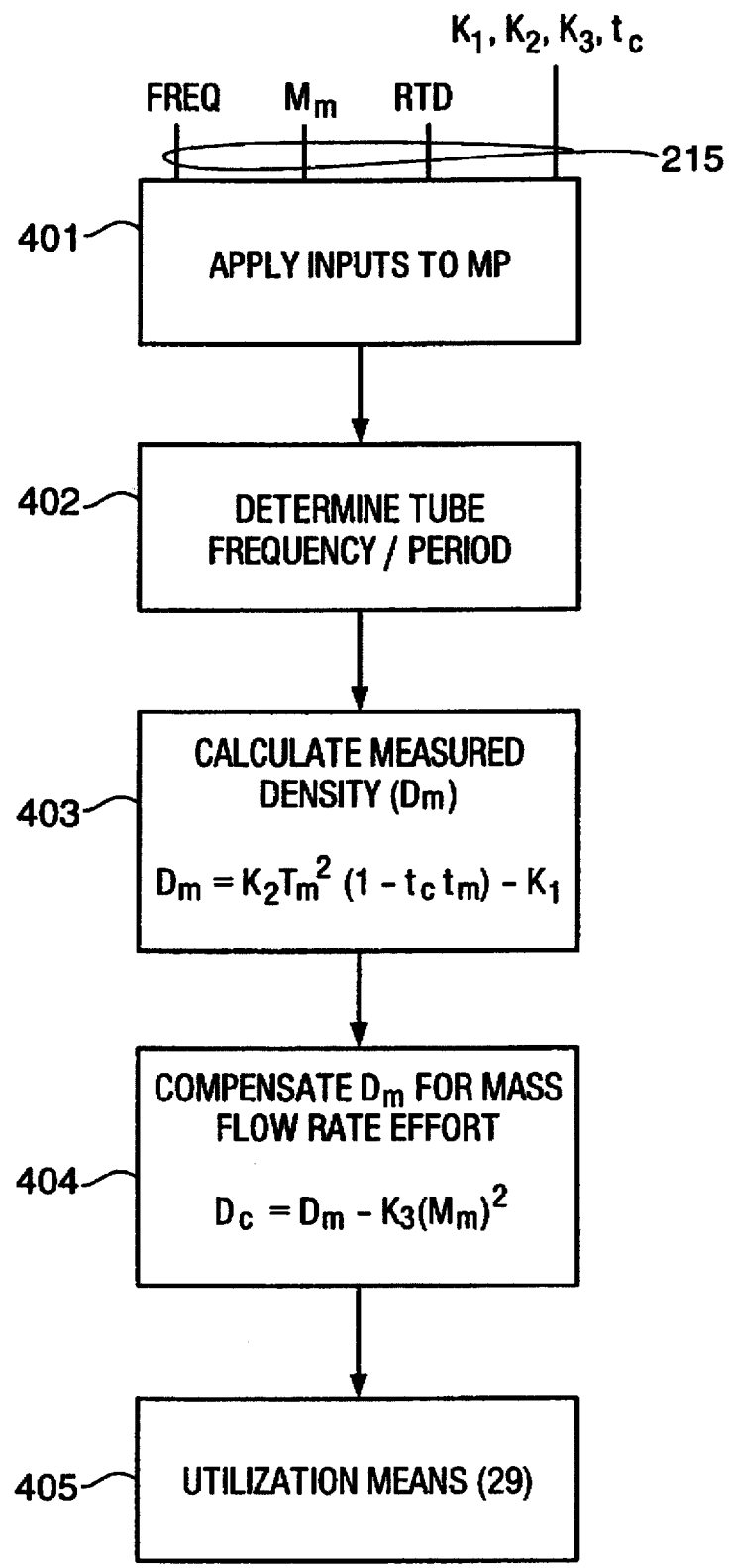
FIG. 4 is a flow chart describing the operation of the meter electronics 20 and its processing circuitry 210 as it measures the density and corrects the measured density for the effect on the density measurement by mass flow rate.

Description of Density Correction (FIG. 4)

FIG. 4 describes in flow chart form how microprocessor 211 and memories 212 and 213 operate in computing a density which is compensated for the effect of mass flow rate on the measured density. A further embodiment of the present invention which additionally compensates for the effect of temperature on the density compensation is discussed below with respect to FIGS. 5 and 6.

During processing step 401 the density measurement process begins with microprocessor 211 receiving input and setup information over system bus 214 from ROM 212, RAM 213 and the inputs to processing circuitry 210 already described. The signals received by microprocessor 211 during this period are the signal representing the frequency of vibration of the flow tubes (FREQ), the temperature signal (RTD), and the measured mass flow rate signal ($M_m$). Also applied to microprocessor 211 during processing step 401 are the constants used by microprocessor 211 in determining the density. These constants, $K_1$, $K_2$, $K_3$ and $t_c$ are stored in ROM 212 and RAM 213 at the time mass flow sensor 10 and meter electronics 20 are calibrated.

Calibration constants $K_1$ and $K_2$ are calculated by determining the period of vibration of the vibrating tube or tubes for two different materials having known densities. The calibration constant $K_3$ is determined by calculating the error in the measured density at a known mass flow rate. This can be done using one of the materials used to determine calibration constants $K_1$ and $K_2$ or a different material can be used. As noted above, $K_1$, $K_2$, and $K_3$ are calculated and stored in memory elements 212 and 213 at the time the densimeter is calibrated.

Calibration constant $t_c$ is related to the Young's modulus of the material of construction of the vibrating tubes. It is known that Young's modulus, which is representative of the stiffness of the tube, changes with temperature. A change in the stiffness of the vibrating tube results in a change in the natural frequency of the vibrating tube. Calibration constant $t_c$ is used, as described below, to compensate for the change in stiffness of the vibrating tube.

During step 402 microprocessor 211 uses the FREQ signal to determine the frequency of vibration of the vibrating tube. Microprocessor 211 also determines the measured tube period ($T_m$) by calculating the reciprocal of the frequency of vibration.

During step 403 microprocessor 411 calculates the measured density ($D_m$) according to the formula:

$$D_m = K_2 T_m^2 (1 - t_c t_m) - K_1$$

where $D_m$ is the measured density of the material (g/cm³)
$T_m$ is the measured tube period (s)
$K_1$ is equal to $K_2 T_a^2 - D_a$
$K_2$ is equal to $d/(T_w - T_a^2)$
$D_w$ is the density of water at the time of calibration (g/cm³)
$D_a$ is the density of air at the time of calibration (g/cm³)
d is $D_w - D_a$ (g/cm³)
$t_c$ is the temperature compensation factor (% change in $T_m^2$/°C.)/100)
$T_a$ is the tube period for air with no flow at the time of calibration, corrected to 0° C. (s)
$T_w$ is the tube period for water with no flow at the time of calibration, corrected to 0° C. (s)
$t_m$ is the measured temperature (°C.)

This calculation of measured density, as well as constants $K_1$, $K_2$, and $t_c$, is the same as that practiced in prior art densimeters such as described by Ruesch.

During step 404 the measured density ($D_m$) is compensated for the effect of mass flow rate to determine a compensated density ($D_c$). The compensated density ($D_c$) is calculated as follows:

$$D_c = D_m - K_3 (M_m)^2$$

where:

$D_m$ is the measured density (g/cm³)
$D_c$ is the compensated density (g/cm³)
$M_m$ is the measured mass flow rate (g)
K3 is equal to $$D_{k3}/M_{k3}^2$$

$D_{k3}$ is the error in the measured density during calibration at a mass flow rate $M_{k3}$ (g/cm³).

During step 405 the compensated density information ($D_c$) is applied to utilization means 29 where it is displayed, recorded, or otherwise utilized in a process control system.

Figure 5:
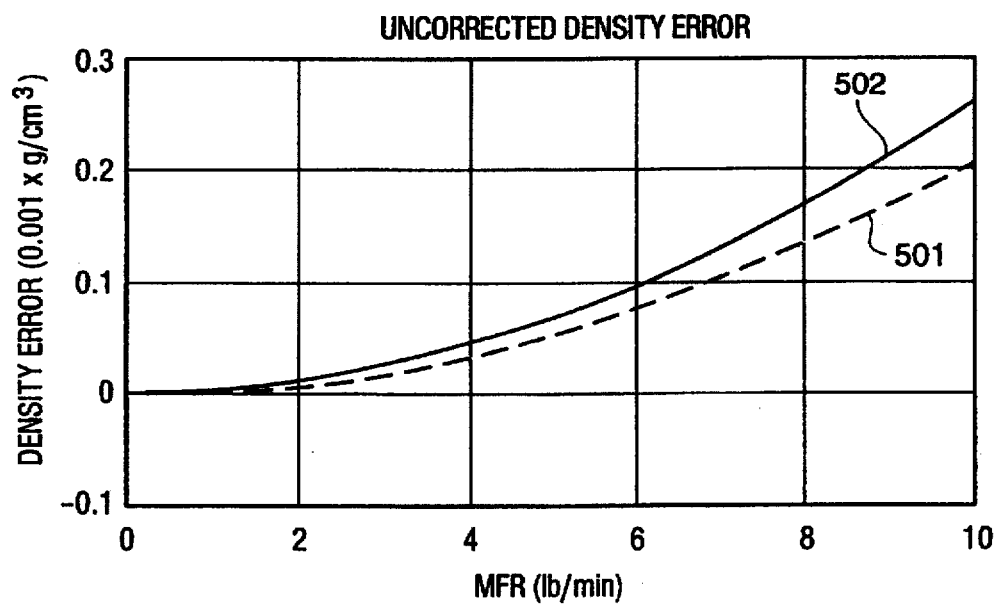
FIG. 5 is a graph illustrating the effect of mass flow rate at various temperatures on the measured density.

Combined Mass Flow Rate and Temperature Effect on Density Measurement (FIG. 5)

In a further embodiment of the present invention, the compensation factor $K_3$ is itself compensated for the effect of the temperature of the tube on the mass flow rate induced density error. Due to the change in Young's Modulus, the mass flow rate will have a slightly different effect on the density measurement at different temperatures of the vibrating tube. This effect is depicted in FIG. 5 where line 501 represents the mass flow rate induced density error in a given densimeter at 30° C. and line 502 represents the mass flow rate induced error in the same densimeter at 100° C. A calibration constant, $K_4$, is developed to compensate for this effect.

$K_4$ is calculated as follows:

$$K_4 = [D_{k4}/(k_3 \times M_{k4}^2) - 1]/(t_{k4} - t_{k3})$$

where $D_{K4}$ is the error in the density reading at temperature $t_{K4}$ and mass flow rate
$M_{K4}$ (g/cc)
$K_3$ is the calibration constant previously defined
$t_{K3}$ is the temperature at which $K_3$ was determined (°C.)
$t_{K4}$ is the temperature at which $K_4$ was determined (°C.)
$M_{K4}$ is the mass flow rate at which $K_4$ was determined (g/s)

$K_4$ is determined during the calibration process in the following manner. After $K_3$ is calculated, material is again passed through the densimeter at a known mass flow rate but this time at a different temperature from the temperature at which $K_3$ was calculated. The density error at this different operating temperature is used as follows to determine $K_4$. Calibration constant $K_4$ is used, as described below, to compensate calibration constant $K_3$ for the effect of temperature on the mass flow rate effect compensation.

Description of Density Correction for Mass Flow Rate Including Temperature Compensation (FIG. 6)

The present invention operates to correct the measured density for the temperature effect on the mass flow rate induced density error in much the same way as was described with respect to FIG. 4. Therefore, the description of FIG. 6 is simplified by describing in detail only those steps that differ from the process described with respect to FIG. 4.

In processing step 601 microprocessor 211 receives all the signals and information described with respect to step 401 of FIG. 4 and in addition receives calibration constant $K_4$ and $t_{k3}$.

In step 602 microprocessor 211 determines the frequency and period of vibration of the vibrating tube as in step 402 of FIG. 4.

In step 603 microprocessor 211 calculates the measured density ($D_m$) as in step 403 of FIG. 4.

In step 604 microprocessor 211 calculates the compensated density ($D_c$) according to the following:

$$D_c = D_m - K_3 (1 + K_4 (t_m - t_{k3}))(M_m)^2$$

where
- $D_m$ is the measured density (g/cc)
- $D_c$ is the corrected density (g/cc)
- $M_m$ is the measured mass flow rate (g/s)
- $t_m$ is the measured temperature
- $t_{k3}$ is the temperature at which $K_3$ was calculated (°C.)
- $K_3$ and $K_4$ as previously defined During step 605 the compensated density information is supplied to utilization means 29 and displayed or used in the same fashion as described with respect to FIG. 4.

The temperature compensation of $K_3$ provided by $K_4$ is linear. The actual dependence of the density error due to mass flow rate on temperature is not simply a linear relationship. It is apparent to those skilled in the art that different compensation factors can be included in $K_4$ to differently characterize the relationship between the density measurement caused by mass flow rate and temperature.

Figure 7:
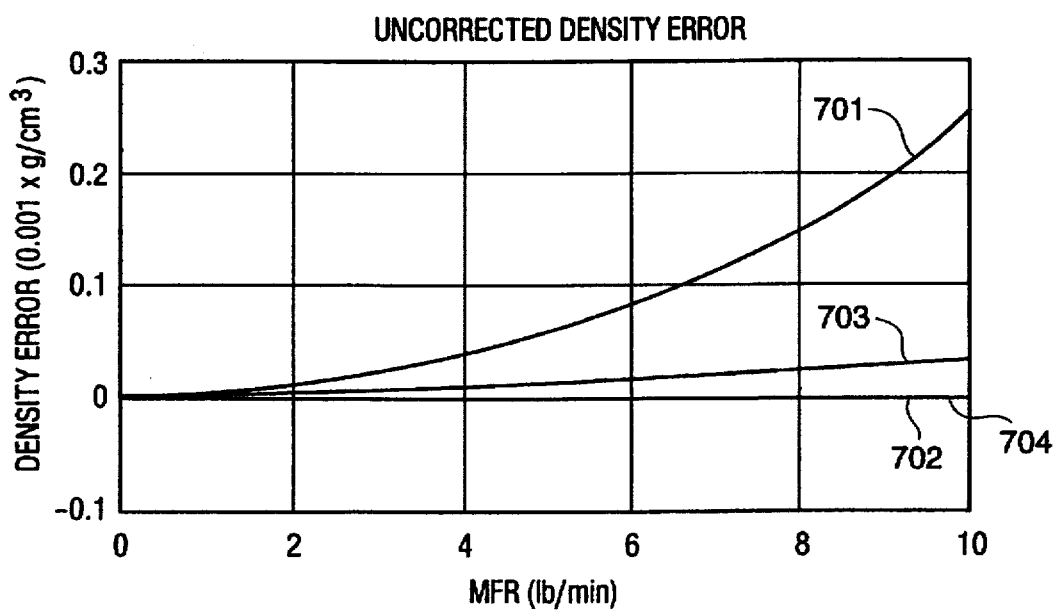
FIG. 7 is a graph illustrating the improvement in density measurement performance with the present invention.

Density Measurement Improvement of the Present Invention (FIG. 7)

FIG. 7 is representative of the improvement in density measurement performance attained with the present invention. The data which make up curves 701–704 are generated from the analytical models discussed above. Curve 701 is representative of the uncorrected error in density measurement. Curve 702 is representative of the error in density measurement utilizing the present invention when the density measurement is made at the same temperature at which the density calibration was performed. Curve 703 is representative of the error in density measurement utilizing only the mass flow rate compensation without the compensation on the mass flow rate compensation for the effect of temperature. The temperature difference, represented by curve 703, between the calibration temperature and the measurement temperature, is 50° C. Curve 704 is representative of the error in density measurement utilizing both the mass flow rate and the temperature compensation portions of the present invention when the measurement temperature is different than that at which the calibration was performed. The temperature difference represented by the data making up curve 704 is the same temperature difference represented by the data making up curve 703.

The advantages of the present invention to the field of density measurement are clear. It is to be expressly understood that the claimed invention is not to be limited to the description of the preferred embodiments but encompasses other modifications and alterations within the scope and spirit of the inventive concept.

Further, the material whose density is determined by the method and apparatus of the present invention may include a liquid, a gas, a mixture thereof, as well as any substance that flows such as slurries of different types. The mass flow rate of the flowing material may be generated by the apparatus comprising the densimeter or, alternatively, can be generated by separate apparatus and applied to the densimeter of the present invention. Likewise, the temperature information utilized by the methods of the present invention can be obtained from a temperature sensor that is part of the densimeter, as described herein, or alternatively can be supplied from some other temperature sensing device.

We claim:

1. A method of operating apparatus for ascertaining the density of material flowing through a flowmeter having vibrating tube means wherein a measured density of said flowing material changes as a flow rate of said flowing material through said vibrating tube means changes: said method comprising the steps of:

measuring the period of vibration of said vibrating tube means as said material flows therethrough, generating a measured density value for said flowing material in response to said measurement of said vibration period, receiving a mass flow rate value representative of said mass flow rate of said flowing material through said vibrating tube, generating a flow rate effect factor defining the sensitivity of said measured density to changes in said mass flow rate of said flowing material;

multiplying said flow rate effect factor by said measured mass flow rate to determine a mass flow rate induced density error value: and reducing said measured density value by an amount substantially equal to said mass flow rate induced density error value to determine said corrected density value; and transmitting said corrected density value to an output device.

2. The method of claim 1 wherein said step of generating said flow rate effect factor comprises the steps of:

measuring a difference between a first calibration density of said flowing material measured at a first calibration mass flow rate and a second calibration density of said flowing material measured at a second calibration mass flow rate, determining, responsive to said measured density difference, said mass flow rate effect factor; and storing said mass flow rate effect factor in a memory.

3. The method of claim 2 wherein said flow rate effect factor is determined by solving the expression $$K_3 = (D1-D2)/(M1-M_2)^2$$

where:

$K_3$ is said flow rate calibration constant, $D_1$ is a first measured density at a first mass flow rate ($M_1$) of said flowing material, $D_2$ is a second measured density ($D_2$) at a second mass flow rate (M2) of said flowing material.

4. The method of claim 1 wherein said corrected density value is determined by solving the expression:

$$D_c = D_m - K_3(M_M)^2$$

where
- $D_c$ is the correct☐ed density,
- $D_M$ is the measured density,
- $K_3$ is said flow rate calibration constant,
- $M_M$ is said measured flow rate.

5. A method according to claim 1 wherein said step of generating a measured density value includes:

calculating, responsive to said measured period of vibration, said measured density value wherein said measured density value is linearly related to the square of said measured period of vibration.

6. The method of claim 5 where said measured density ($D_M$) is determined by solving the expression:

$$D_m = K_2 T_m^2 (1-t_c t_m) - K_1$$

where
- $D_m$ is the measured density of the material (g/cm$^3$)
- $T_m$ is the measured tube period (s)

$K_1$ is equal to $K_2T_a^2-D_a$ $K_2$ is equal to $d/(T_w^2-T_a^2)$ $D_w$ is the density of water at the time of calibration (g/cm³)

$D_a$ is the density of air at the time of calibration (g/cm³)

d is $D_w-D_a$ (g/cm³)

$t_c$ is the temperature compensation factor ((% change in $T^2_m/°C.)/100$)

$T_a$ is the tube period for air with no flow at the time of calibration, corrected to 0° C. (s)

$T_w$ is the tube period for water with no flow at the time of calibration, corrected to 0° C. (s)

$t_m$ is the measured temperature (°C.).

7. A method according to claim 1, wherein said step of calculating a corrected density value includes the steps of:

retreiving a flow rate effect factor for said flowmeter from a memory, wherein said flow rate effect factor defines a sensitivity of said measured density with respect to said mass flow rate of said flowing material, receiving a temperature value wherein said temperature value is representative of the temperature of said flowing material, adjusting, responsive to said temperature value, said flow rate effect factor; and applying said temperature adjusted flow rate effect factor to said measured density to determine said corrected density.

8. A method according to claim 7 wherein said step of adjusting said flow rate effect factor includes:

retrieving a temperature compensation factor from a second memory wherein said temperature compensation factor defines a sensitivity of said flow rate effect factor with respect to changes in temperature of said flowing material; and applying said temperature compensation factor to said flow rate effect factor to adjust said flow rate effect factor for the effect of a change in temperature of said flowing material.

9. A method acording to claim 8 wherein said temperature compensation factor is determined by solving the expression:

$$K_4=[D_{k4}/(K_3 \times M_{k4}^2)-1]/(t_{k4}-t_{k3})$$

where $D_{K4}$ is the error in the measured density ($D_m$) at temperature $t_{K4}$ and mass flow rate $M_{K4}$ $K_3$ is the calibration constant previously defined $t_{K3}$ is the temperature at which $K_3$ was determined (°C.)

$t_{K4}$ is the temperature at which $K_4$ was determined (°C.)

$M_{K4}$ is the mass flow rate at which $K_4$ was determined (g/s).

10. A method according to claim 9 wherein said step of applying said temperature adjusted flow rate effect factor to said measured density and said measured mass flow rate includes solving the expression:

$$D_c=D_m-K_3(1+K_4(t_m-t_{k3}))(M_m)^2$$

where:

$D_m$ is the measured density (g/cc)

$D_c$ is the corrected density (g/cc)

$M_m$ is the measured mass flow rate (g/s)

$t_m$ is the measured temperature (°C.)

$t_{k3}$ is the temperature at which $K_3$ was calculated (°C.)

$K_3$ and $K_4$ as previously defined.

11. A machine readable storage device, tangibly embodying instructions executable by a computer to perform method steps for ascertaining the density of material flowing through a flowmeter having vibrating tube means wherein a measured density of said flowing material changes as a flow rate of said flowing material through said vibrating tube means changes, said method steps comprising:

measuring the period of vibration of said vibrating tube means as said material flows therethrough, generating a measured density value for said flowing material in response to said measurement of said vibration period, receiving a mass flow rate value representative of said mass flow rate of said flowing material through said vibrating tube, generating a flow rate effect factor defining the sensitivity of said measured density to changes in said mass flow rate of said flowing material;

multiplying said flow rate effect factor by said measured mass flow rate to determine a mass flow rate induced density error value;

reducing said measured density value by an amount substantially equal to said mass flow rate induced density error value to determine said corrected density value; and transmitting said corrected density value to an output device.

12. The method of claim 11 wherein said step of generating said flow rate effect factor comprises the steps of:

measuring a difference between a first calibration density of said flowing material measured at a first calibration mass flow rate and a second calibration density of said flowing material measured at a second calibration mass flow rate, determining, responsive to said measured density difference, said mass flow rate effect factor; and storing said mass flow rate effect factor in a memory.

13. The method of claim 12 wherein said flow rate effect factor is determined by solving the expression $$K_3=(D1-D2)/(M1-M2)^2$$

where:

$K_3$ is said flow rate calibration constant, $D_1$ is a first measured density at a first mass flow rate ($M_1$) of said flowing material, $D_2$ is a second measured density ($D_2$) at a second mass flow rate ($M_2$) of said flowing material.

14. The method of claim 11 wherein said corrected density value is determined by solving the expression:

$$D_c=D_M-K_3(M_M)^2$$

where $D_c$ is the correct☐ed density, $D_M$ is the measured density, $K_3$ is said flow rate calibration constant, $M_M$ is said measured flow rate.

15. A method according to claim 11 wherein said step of generating a measured density value includes:

calculating, responsive to said measured period of vibration, said measured density value wherein said measured density value is linearly related to the square of said measured period of vibration.

16. The method of claim 15 where said measured density ($D_M$) is determined by solving the expression:

$$D_m = K_2 T_m^2 (1 - t_c t_m) - K_1$$

where $D_m$ is the measured density of the material (g/cm³)

$T_m$ is the measured tube period (s)

$K_1$ is equal to $K_2 T_a^2 - D_a$ $K_2$ is equal to $d/(T_w^2 - T_a^2)$ $D_w$ is the density of water at the time of calibration (g/cm³)

$D_a$ is the density of air at the time of calibration (g/cm³)

d is $D_w - D_a$ (g/cm³)

$t_c$ is the temperature compensation factor ((% change in $T^2_m/°C.)/100$)

$T_a$ is the tube period for air with no flow at the time of calibration, corrected to 0°C. (s)

$T_w$ is the tube period for water with no flow at the time of calibration, corrected to 0° C. (s)

$t_m$ is the measured temperature (°C.).

17. A method according to claim 11, wherein said step of calculating a corrected density value includes the steps of:

retreiving a flow rate effect factor for said flowmeter from a memory, wherein said flow rate effect factor defines a sensitivity of said measured density with respect to said mass flow rate of said flowing material, receiving a temperature value wherein said temperature value is representative of the temperature of said flowing material, adjusting, responsive to said temperature value, said flow rate effect factor; and applying said temperature adjusted flow rate effect factor to said measured density to determine said corrected density.

18. A method according to claim 17 wherein said step of adjusting said flow rate effect factor includes:

retrieving a temperature compensation factor from a second memory wherein said temperature compensation factor defines a sensitivity of said flow rate effect factor with respect to changes in temperature of said flowing material; and applying said temperature compensation factor to said flow rate effect factor to adjust said flow rate effect factor for the effect of a change in temperature of said flowing material.

19. A method acording to claim 18 wherein said temperature compensation factor is determined by solving the expression:

$$K_4 = [D_{k4}/(K_3 \times M_{k4}^2) - 1]/(t_{k4} - t_{k3})$$

where $D_{K4}$ is the error in the measured density ($D_m$) at temperature $t_{k4}$ and mass flow rate $M_{K4}$, $K_3$ is the calibration constant previously defined $t_{K3}$ is the temperature at which $K_3$ was determined (°C.)

$t_{K4}$ is the temperature at which $K_4$ was determined (°C.)

$M_{K4}$ is the mass flow rate at which $K_4$ was determined (g/s).

20. A method according to claim 19 wherein said step of applying said temperature adjusted flow rate effect factor to said measured density and said measured mass flow rate includes solving the expression:

where:

$D_m$ is the measured density (g/cc)

$D_o$ is the corrected density (g/cc)

$M_m$ is the measured mass flow rate (g/s)

$t_m$ is the measured temperature (°C.)

$t_{k3}$ is the temperature at which $K_3$ was calculated (°C.)

$K_3$ and $K_4$ as previously defined.

21. An apparatus for ascertaining the density of material flowing through a flowmeter having vibrating tube means wherein a measured density of said flowing material changes as a flow rate of said flowing material through said vibrating tube means changes, said apparatus comprising:

means for measuring the period of vibration of said vibrating tube means as said material flows therethrough, means for generating a measured density value for said flowing material in response to said measurement of said vibration period, means for receiving a mass flow rate value representative of said mass flow rate of said flowing material through said vibrating tube, means for generating a flow rate effect factor defining the sensitivity of said measured density to changes in said mass flow rate of said flowing material;

means for multiplying said flow rate effect factor by said measured mass flow rate to determine a mass flow rate induced density error value;

means for reducing said measured density value by an amount substantially equal to said mass flow rate induced density error value to determine said corrected density value; and means for transmitting said corrected density value to an output device.

22. The apparatus of claim 21 wherein said means for generating said flow rate effect factor includes:

means for measuring a difference between a first calibration density of said flowing material measured at a first calibration mass flow rate and a second calibration density of said flowing material measured at a second calibration mass flow rate, means for determining, responsive to said measured density difference, said mass flow rate effect factor, and means for storing said mass flow rate effect factor in a memory.

23. The apparatus of claim 22 wherein said flow rate effect factor is determined by solving the expression $$K_3 = (D1 - D2)/(M1 - M_2)^2$$

where:

$K_3$ is said flow rate calibration constant, $D_1$ is a first measured density at a first mass flow rate ($M_1$) of said flowing material, $D_2$ is a second measured density ($D_2$) at a second mass flow rate (M2) of said flowing material.

24. The apparatus of claim 21 wherein said corrected density value is determined by solving the expression:

$$D_C = D_M - K_3(M_M)^2$$

where $D_C$ is the correct☐ed density, $D_M$ is the measured density, $K_3$ is said flow rate calibration constant, $M_M$ is said measured flow rate.

25. The apparatus according to claim 21 wherein said means for generating a measured density value includes:

means for calculating, responsive to said measured period of vibration, said measured density value wherein said measured density value is linearly related to the square of said measured period of vibration.

26. The apparatus of claim 25 where said measured density ($D_M$) is determined by solving the expression:

$$D_m = K_2 T_m^2 (1 - t_c t_m) - K_1$$

where $D_m$ is the measured density of the material (g/cm$^3$)

$T_m$ is the measured tube period (s)

$K_1$ is equal to $K_2 T_a^2 - D_a$ $K_2$ is equal to $d/(T_w^2 - T_a^2)$ $D_w$ is the density of water at the time of calibration (g/cm$^3$)

$D_a$ is the density of air at the time of calibration (g/cm$^3$)

d is $D_w - D_a$ (g/cm$^3$)

$t_c$ is the temperature compensation factor ((% change in $T_m^2$/°C.)/100)

$T_a$ is the tube period for air with no flow at the time of calibration, corrected to 0° C. (s)

$T_w$ is the tube period for water with no flow at the time of calibration, corrected to 0° C. (s)

$t_m$ is the measured temperature (°C.).

27. The apparatus according to claim 21, wherein said means for calculating a corrected density value includes:

means for retreiving a flow rate effect factor for said flowmeter from a memory, wherein said flow rate effect factor defines a sensitivity of said measured density with respect to said mass flow rate of said flowing material, means for receiving a temperature value wherein said temperature value is representative of the temperature of said flowing material, means for adjusting, responsive to said temperature value, said flow rate effect factor; and means for applying said temperature adjusted flow rate effect factor to said measured density to determine said corrected density.

28. An apparatus according to claim 27 wherein said means for adjusting said flow rate effect factor includes:

means for retrieving a temperature compensation factor from a second memory wherein said temperature compensation factor defines a sensitivity of said flow rate effect factor with respect to changes in temperature of said flowing material; and means for applying said temperature compensation factor to said flow rate effect factor to adjust said flow rate effect factor for the effect of a change in temperature of said flowing material.

29. An apparatus acording to claim 28 wherein said temperature compensation factor is determined by solving the expression:

$$K_4 = [D_{k4}/(K_3 \times M_{k4}^2) - 1]/(t_{k4} - t_{k3})$$

where $D_{K4}$ is the error in the measured density ($D_m$) at temperature $t_{K4}$ and mass flow rate $M_{K4}$ $K_3$ is the calibration constant previously defined $t_{K3}$ is the temperature at which $K_3$ was determined (°C.)

$t_{K4}$ is the temperature at which $K_4$ was determined (°C.)

$M_{K4}$ is the mass flow rate at which $K_4$ was determined (g/s).

30. An apparatus according to claim 29 wherein said means for applying said temperature adjusted flow rate effect factor to said measured density and said measured mass flow rate includes solving the expression:

$$D_c = D_m - K_3(1 + K_4(t_m - t_{k3}))(M_m)^2$$

Where:

$D_m$ is the measured density (g/cc)

$D_c$ is the corrected density (g/cc)

$M_m$ is the measured mass flow rate (g/s)

$t_m$ is the measured temperature (°C.)

$t_{k3}$ is the temperature at which $K_3$ was calculated (°C.)

$K_3$ and $K_4$ as previously defined.

* * * * *